United States Patent [19]
Pennig

[11] Patent Number: 5,443,465
[45] Date of Patent: Aug. 22, 1995

[54] OSTEOSYNTHESIS AID

[76] Inventor: Dietmar Pennig, Hans-Driesch-Strasse 12, 50935, Köln, Germany

[21] Appl. No.: 123,302
[22] Filed: Sep. 17, 1993
[30] Foreign Application Priority Data
Sep. 19, 1992 [DE] Germany .................. 42 31 443.7
[51] Int. Cl.6 ............................................. A61B 17/60
[52] U.S. Cl. .................................. 606/59; 606/54; 606/72
[58] Field of Search .......... 606/54, 55, 57, 58, 606/59, 53, 72, 105; 279/6

[56] References Cited

U.S. PATENT DOCUMENTS

| | | | |
|---|---|---|---|
| 4,098,269 | 7/1978 | Judet | 606/54 |
| 4,244,360 | 1/1981 | Dohogne | 606/59 |
| 4,299,212 | 11/1981 | Goudfrooy | 606/54 |
| 4,312,336 | 1/1982 | Danieletto et al. | 606/59 |
| 4,621,627 | 11/1986 | DeBastiani et al. | 606/54 |
| 4,895,141 | 1/1990 | Koeneman et al. | 606/54 |
| 5,112,340 | 5/1992 | Krenkel et al. | 606/130 |
| 5,312,403 | 5/1994 | Frigg | 606/54 |
| 5,320,622 | 6/1994 | Faccioli et al. | 606/58 |

FOREIGN PATENT DOCUMENTS

| | | |
|---|---|---|
| 2301222 | 9/1976 | France . |
| 2557933 | 7/1985 | France . |
| 2673835 | 9/1992 | France . |
| 3805178 | 8/1989 | Germany ............... 606/54 |
| 2101488 | 1/1983 | United Kingdom . |
| 2229096 | 9/1990 | United Kingdom . |

Primary Examiner—Stephen C. Pellegrino
Assistant Examiner—Guy Tucker

[57] ABSTRACT

The invention refers to an osteosynthesis aid which is used, in particular, for the fixation of a pelvis and includes a central body which is formed of at least two arm or link members, each of which has an elongate slot through which a lock bolt is passed to provide a releasably clamped joint and each of which also has releasably secured ball-joint connection to an end-connecting clamp for bone-pin or bone-screw anchorage to an afflicted bone.

10 Claims, 4 Drawing Sheets

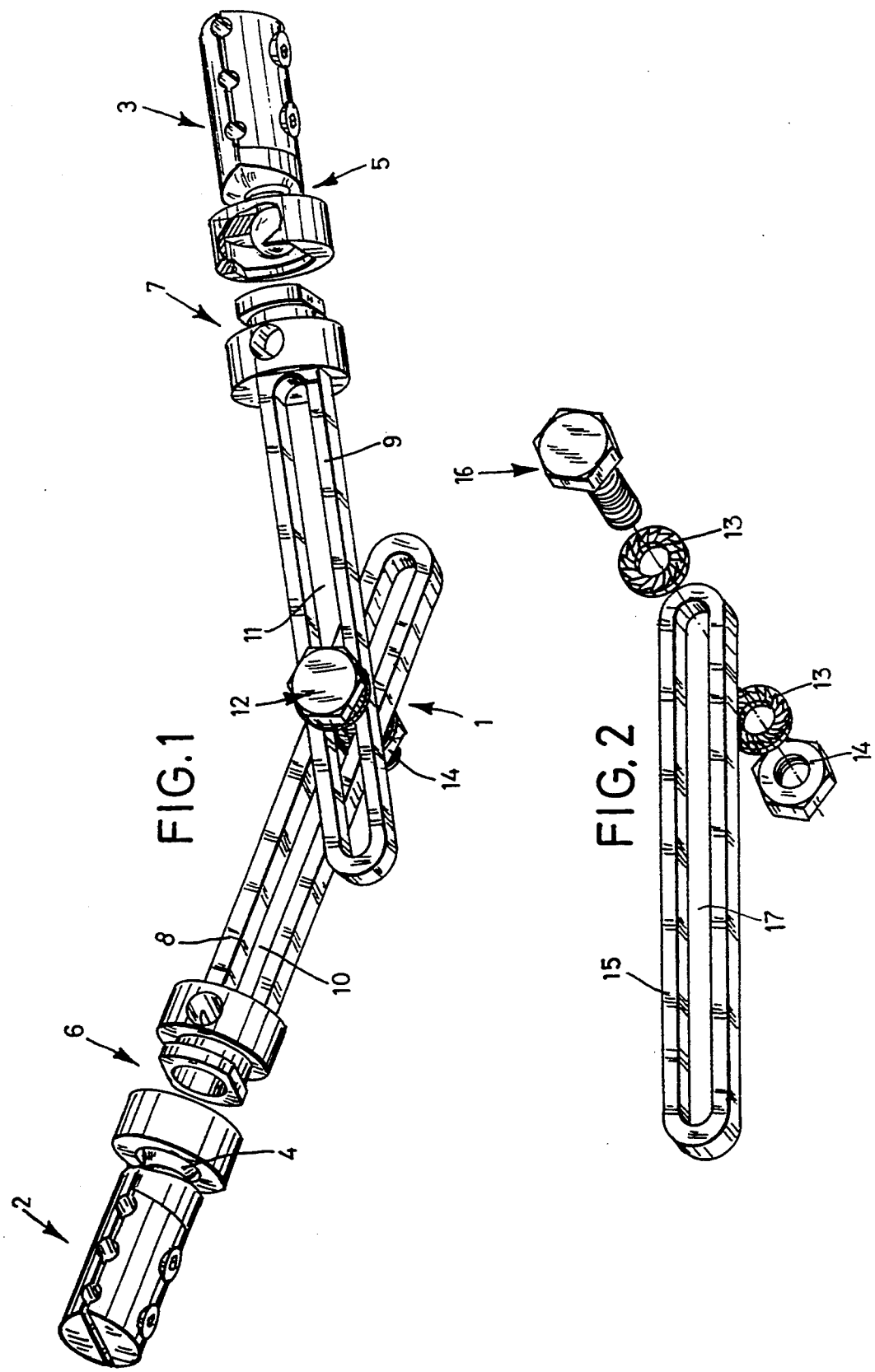

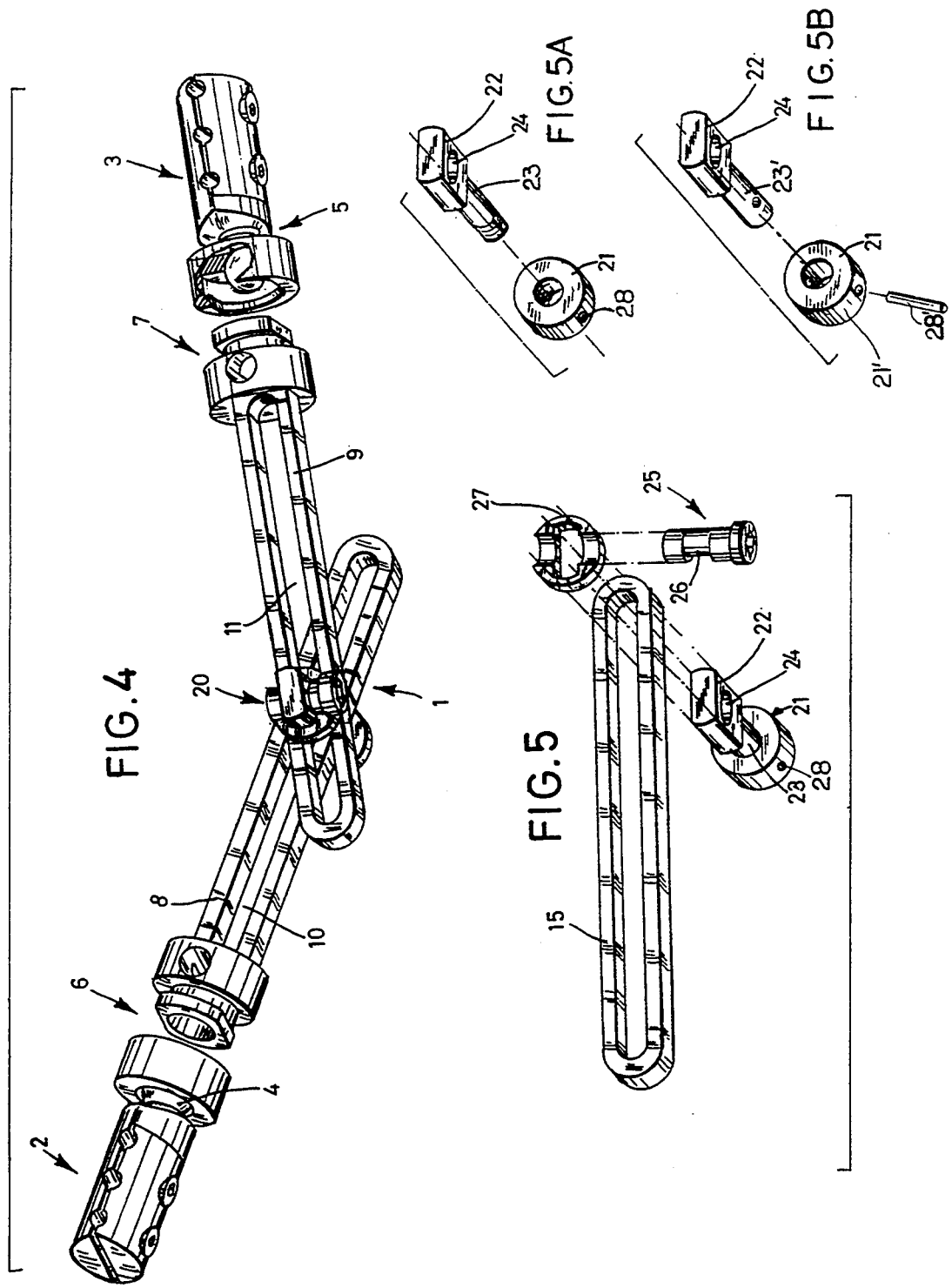

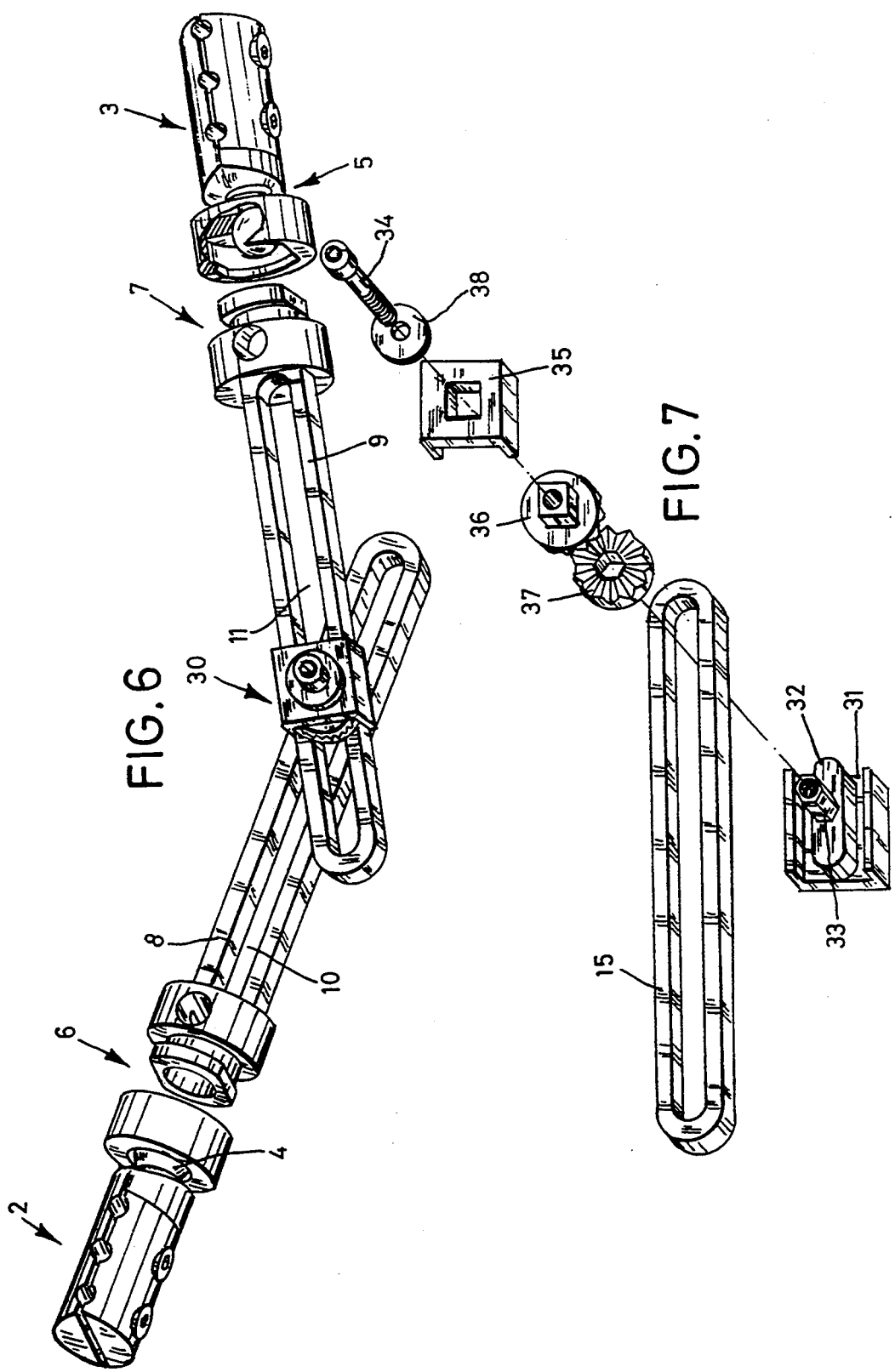

5,443,465

OSTEOSYNTHESIS AID

BACKGROUND OF THE INVENTION

The present invention pertains to an osteosynthesis aid for bone fixation, particularly for application to pelvic-bone structure.

German Patent No. 3,917,916 C1 discloses and describes an external fixation device, particularly for application to the pelvis. The device comprises two bone-pin or screw-holding clamps, and these clamps are ball-joint connected and selectively clamped to a central body. The central body consists of two pivotally connected elongate arms each of which has telescopically guided parts which provide a measure of arm-length adjustability. The telescopic adjustments and the pivotal connection of the arms are both releasably securable to hold given adjustment thereof.

The known device is rather expensive and has a limited range of length adjustability, so that several different sizes must be kept in stock in order to provide the surgeon with the proper osteosynthesis aid for a specific case of use.

BRIEF STATEMENT OF THE INVENTION

The principal object of the invention is to provide an osteosynthesis aid for use in connection with pelvic bones, offering a great range of possible releasably locked adjustment but of simple low-cost construction; and it is also an object to provide in such a simple device for the previously available feature of selectively adjusted articulation. A specific object is to provide improved releasably lockable means for positive retention of any desired adjustment.

The invention achieves these objects with a fixator of releasably lockable the character indicated wherein the central body, between ball-joint connected bone-pin or screw clamps, comprises two elongate link members or arms each of which has an elongate slot; and a lock bolt through both slots (i.e., through the slot of each arm or link) serves the combined purpose of selectively locking the central body for overall length between ball-joint connections and for a selected angular relation between the respective arms. A further elongate and slotted link is optionally usable with a second lock bolt to provide further length and bowed adjustment upon lock-bolt connection of the link to each of the respective ball-joint connected arm members.

More specifically, each of the ball-joint equipped arms has a slot which extends preferably over virtually the entire length of the arm, into proximity with the associated bone-pin or screw holding clamps, and the fixation of these holding clamps is effected via lock-bolt connection of the arms. Thus, the arms can be pushed together to a minimum overall length dimension, wherein the fixation devices are in near-contact with each other, and they can also be pulled apart to a maximum size such that the lock bolt establishes a limit stop at the other slot extremes. In this way, substantially greater changes in length are possible than in the prior art, while at the same time the entire device is of extremely economical construction, so that a two-fold advantage is obtained, namely, on the one hand, fewer individual parts are necessary and, on the other hand, the manufacture of the device is less expensive. Furthermore, one lock-bolt setting serves to retain a length adjustment and a selected pivoted or articulation-angle setting of the slotted arms with respect to each other. Various lock-bolt configurations are described.

BRIEF DESCRIPTION OF THE DRAWINGS

Preferred embodiments of the invention will be described in detail in conjunction with the accompanying drawings, in which:

FIG. 1 is a partly exploded view in perspective of a fixator device of the invention, featuring a first selectively operable locking device;

FIG. 2 is a similar view of optional connection-link components usable with the fixator of FIG. 1, with an exploded showing of the locking device of FIG. 1;

FIG. 4 is a view similar to FIG. 1, to show a different locking device;

FIG. 5 is a view similar to FIG. 2, with an exploded showing of the locking device of FIG. 4;

FIG. 5A is an exploded view of dissassembled elements of one of the parts of FIG. 5;

FIG. 5B is a view similar to FIG. 5A to show a modified construction;

FIG. 6 is another view similar to FIG. 1, to show another different locking device; and FIG. 7 is another view similar to FIG. 2, with an exploded showing of the locking device of FIG. 6.

DETAILED DESCRIPTION

Figure 3:
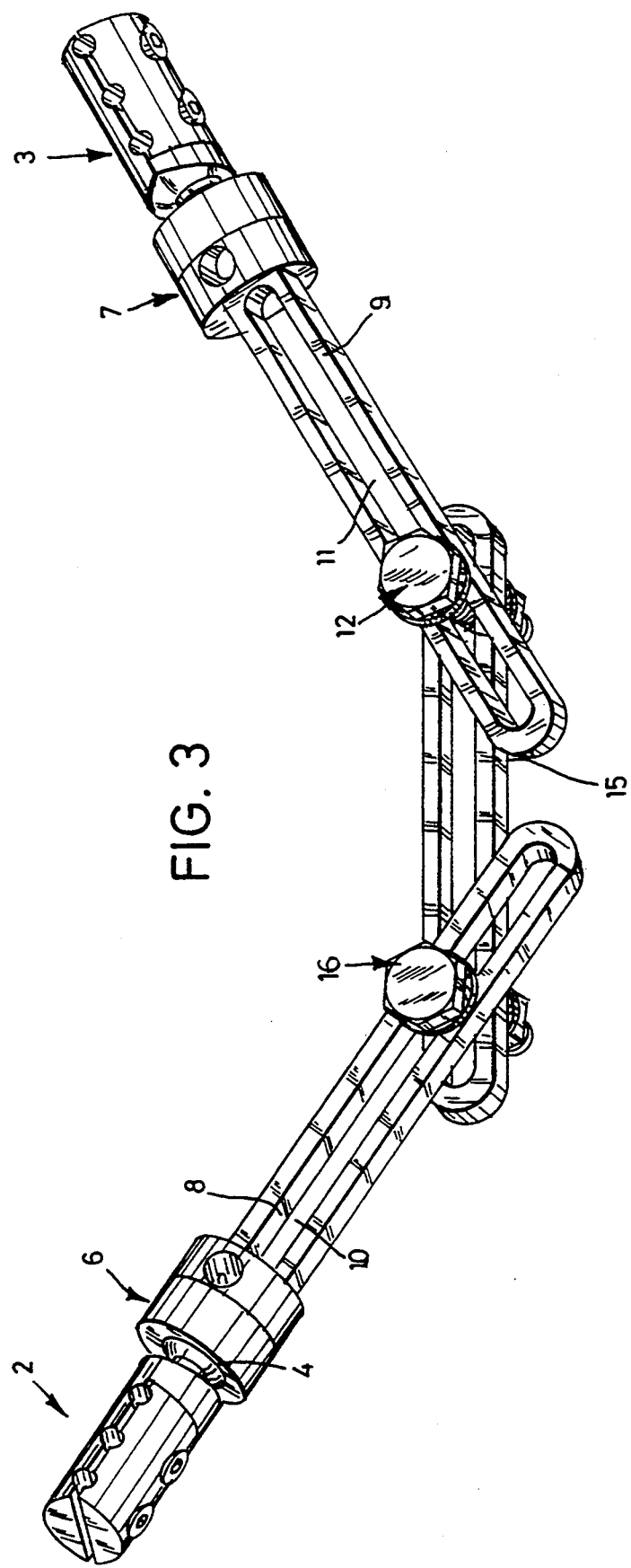
FIG. 3 is a perspective view of the complete fixator, to show an assembly of the parts of FIGS. 1 and 2.

In FIG. 1, an osteosynthesis aid or external fixator device is shown with two bone-pin or screw holding clamps 2, 3 of known construction, and ball joints 4 and 5, with detachable securing devices 6 and 7 by which to establish interconnection via a central body 1; the devices 4/6 and 5/7 will each be understood to constitute a releasably lockable ball joint, providing an adjustably secured angular relation between the elongation axis of each pin or screw holding clamp 2 (3) and the longitudinal axis of the adjacent end of body 1.

The detachable securing devices 6 and 7 are also of known construction, so that their further description is unnecessary.

The central body 1 consists of two elongate arms or links in the form of narrow rigid members, each having a slot (10, 11) which extends over substantially the entire length of each arm, one end of each arm being formed with part of an associated detachable securing device (6, 7) and the other end of each arm being closed around the end of its slot (10, 11). When arms 8, 9 are caused to intersect one above the other as shown in FIG. 1, the respective slots (10, 11) establish adjustable passage for the bolt 12 of a lock-bolt mechanism, consisting of a machine bolt 12 and a nut 14, preferably with interposed friction or lock washers 13 at seating bolt-head and nut engagement with the respective arms 8, 9.

It can be seen that the pin or screw holding clamps 2 and 3 and the securing devices 6 and 7 can now be adjusted to such proximity that the securing devices 6 and 7 practically touch each other and that, on the other hand, these structural parts can be pulled apart to such an extent that the lock bolt 12 passes through the extreme ends of slots 10, 11, i.e., at the ends most remote from securing devices 6 and 7. Also, upon tightening the bolt to the nut, via the lock washers as described, not only is the selected length secured (as between the ball joints 4, 5) but so also is the selected angular relation between arms 8 and 9.

For even greater spacing of the locations of bone-pin or screw clamping, the described fixator device of FIG. 1 is part of a kit which additionally includes the parts of FIG. 2, namely, an elongate link member 15 having a slot 17 extending substantially the full longitudinal extent of link member 15, as well as an additional lock-bolt mechanism 16, identical to that at 12 in FIG. 1. FIG. 3 shows an interconnected use of the parts of FIGS. 1 and 2, with the selective availability of bone-anchorage points (via holding clamps 2, 3) at extended spacing and bowed interconnection, so that a fixation of pelvis regions can be effected even for a patient with a large abdomen.

Merely for the sake of completeness, it is pointed out that the fixing of the pin or screw holding clamps (2, 3) is preferably established between the upper and the lower anterior iliac spine or iliac crest.

FIGS. 4 and 5 show adjustably linked structures as in FIGS. 1 and 2, except for the use of a different locking means 20 to retain an adjusted setting, as to length and as to angle between thus-connected members.

The lock-bolt mechanism 20 is seen in FIGS. 5 and 5A to comprise four parts wherein wrenched actuation of an eccentric surface releasably sets the mechanism. The four parts are (i) a headed pin assembly of two parts, namely, a disc or head part 21, and a cylindrical shank portion 23 with an enlarged distal end 22 of generally rectangular section, featuring a transverse bore 24 through the thickness of said section; (ii) a circular clamp seat or washer 27 featuring a bore configured for non-rotatable but axially guided reception of the generally rectangular section of the distal end 22 of the headed pin, and also featuring like cylindrically arcuate bearing grooves on opposite sides of the width dimension of the bore 24 of distal end 22; and (iii) a transverse eccentric-locking pin 25 having spaced cylindrical bearings sized to pass through the transverse bore 24 of the headed pin 21 and to derive rotational support from the bearing grooves of the clamp seat or washer 27, with the eccentric formation 26 of pin 25 located between the spaced cylindrical bearings.

More specifically, the width dimension of the enlarged distal end 22 of pin 21 is such as to permit slidable insertion through the longitudinal slots of either of two link members to be clamped, and a generally rectangular central opening in washer 27 will also be seen to accommodate keyed insertion of distal end 22.

The effective longitudinal length of the cylindrical shank portion 23 should be such as to assure that the enlarged distal end 22 will engage the longitudinal slot of one to the exclusion of the other of the link members to be clamped, thereby permitting free link-member articulation prior to clamping. As seen in FIG. 5A, the cylindrical shank portion 23 has a lower end adapted for threaded engagement to a tapped central bore of the head part 21; in initial but incomplete assembly of shank 23 to head part 21, the threaded engagement is to a point short of final or fully-threaded engagement, substantially to the axial extent of the throw of the eccentric. Clamped assembly is completed by inserting the eccentric-locking pin 25 through the transverse bore 24, with the spaced bearings of pin 25 nested in the spaced bearing grooves of washer 27, and with the eccentric of pin 25 displaced maximally in the direction of the loosely threaded engagement of shank 23 to the head or disc part 21. In this condition, the parts will be understood to be loosely assembled, permitting slot-positioning selection and angular adjustment of the involved link members. Thereafter, the threaded engagement is advanced to completion and is preferably retained, as by suitable set-screw means, suggested at 28, whereby the clamping action may be releasably established by wrenched rotation of pin 25, to cause its eccentric surface to jam the parts via eccentric action on the transverse bore 24.

In the modification of FIG. 5B, parts are as described for FIG. 5A except that the cylindrical shank portion 23' is sized for slidable fit to the smooth central bore of the head or disc part 21'. The shank portion 23' has a transverse-pin bore which will register with a transverse-pin bore in disc part 21', once the eccentric region of locking pin 25 is correctly positioned in the transverse bore 24. At that time, a transverse pin 28' driven through the aligned transverse bores of disc part 21' and shank portion 23' will retain the parts in readiness for releasable clamping of the involved link members, via wrench-driven rotation of the eccentric-locking pin 25.

In the embodiment of FIGS. 6 and 7, the lock-bolt assembly 30 involves six parts, in addition to the two link members 8, 9 which are to be adjustably set and clamped for angular relation and for span between their respective ball-joint centers at 4 and 5. In FIG. 7, these individual parts are:

(i) a lower slide member 31, shown as a channel with side plates for guidance along outer sides of one to the exclusion of the other of the two link members to be clamped; and with an elongate central pedestal 32 rising from the channel base for further stabilization of guidance solely in the elongate slot of said one link member. An upstanding column 33 of hexagonal section (and having a tapped central bore) rises integrally from pedestal 32 and is of sufficient length to extend through the combined thickness of the two link members to be clamped, and to extend a short distance beyond, for a keying purpose which will be explained;

(ii) a pair of locking disc members 37, 36 having confronting faces with complimentary plural tooth formations in angularly distributed array in order to physically lock the angular relation of disc members 37, 36 when axially clamped together. In FIG. 7, the lower one (37) of these disc members will be understood to have a flat annular surface sized for clamped seating on both legs of the upper one of the involved two link members to be clamped, as in the case of link member 9 of FIG. 6; this disc member 37 also has a central bore of hexagonal section to engage column 33 and to key the same against rotation with respect to the lower slide 31 and, hence, also with respect to the lower link member (e.g., member 8) to be clamped. The upper one (36) of the toothed disc members has a flat upper surface from which a central projection of square section rises to an extent sufficient to establish its keyed relation with an upper slide member 35.

(iii) the upper slide member 35 is also shown as a channel with side plates, for guidance solely along outer sides of the other link member (e.g., upper link member 9 in FIG. 6). The base of the channel of slide member 35 has a central opening of square shape to receive the square projection of the upper one (36) of the toothed discs, thereby completing the keyed relation noted above for these two parts.

(iv) a wrenchable bolt 34 and seating washer 38 complete the recital of parts, it being noted that upon assembly of the described parts of lock bolt 30, the shank of bolt 34 passes freely through central openings in washer 38, slide 35, and the toothed discs 36, 37, with threaded engagement solely to the tapped bore of column 32 of the lower slide 32.

Thus, for the lock-bolt configuration of FIG. 7 in use at 30, in the combination shown in FIG. 6, it is possible to obtain any desired angular adjustment of link members 8, 9, within the number of tooth-engageable relations as between discs 36, 37. And, whatever the selected angular relationship, a wrenched setting of bolt 35 engagement to the tapped bore of slide 31, will establish an absolute lock of the involved link members. The same availability of a locked-up angular relation is also achievable whenever link member 15 is selected for interconnection to the respective ball-joint equipped link members 8, 9, wherein lock bolts 30 are used in replacement of the locking bolts 12 and 16 of FIG. 3.

It will be understood that, for convenience, the expression "lock bolt" or "lock-bolt mechanism" has been used in connection with devices 20 (FIG. 4) and 30 (FIG. 6), even though they are not conventional nut and bolt configurations. And it will be noted that, for all disclosed embodiments, the particularly involved "lock-bolt mechanism" incorporates its own means of locked engagement to each of the two link members thereby secured to each other. This result is achieved without any special upper or lower surface roughening of either of the arm members that are lock-bolt secured, so that the surfaces of all arm members (8, 9, 15) need not be but preferably are of frictionally engageable finish throughout. And in the case of means 30 (FIG. 6), the angularly adjusted lock-up establishes a positively keyed relation of the involved arm members.

What is claimed is:

1. An osteosynthesis device for fixation of a fractured pelvis, comprising a central multi-part body of variable length between spaced ends of said body, first and second bone-pin or screw clamps having releasably lockable ball-joint connection to the respective ends of said body, said body comprising two interconnectable arm or link members each of which has an elongate slot, and lock-bolt connection means through the slot of said arm or link members, said lock-bolt connection means comprising a shank of length to exceed passage through the slot of each of said arm or link members to be connected, a head at one end of the shank and of diametral extent exceeding the width of the arm or link-member slot adjacent thereto, said shank having a cylindrical portion extending through the thickness of the arm or link member adjacent said head, said shank being enlarged and configured distally of said cylindrical portion for keying engagement with at least a portion of the other arm or link member and distally projecting beyond said other arm or link member; and locking means including a seating washer of width exceeding the slot width of the other arm or link member with the distal end of said shank projecting beyond said seating washer, a transverse rotatable pin that is centrally engaged to the distally projecting end of said shank and that has cylindrical bearing portions eccentric to the central engagement, said bearing portions riding diametrically opposite portions of said washer.

2. An osteosynthesis aid according to claim 1, in which the number of said interconnectable arm or link members is at least three, two of which have the body-end connections to said bone-pin or screw clamps, at least one of said arm or link members being a link having an elongate slot between closed longitudinal ends, and in which said lock-bolt connection means is one of two, for selective locking of said link to the respective two members which have said body-end connections to said clamps.

3. An osteogenic device according to claim 1, in which an interconnection link has a first lock-bolt connection via slot of one of said arm or link members and a second lock-bolt connection via the slot of the other of said arm or link members.

4. An osteosynthesis device according to claim 3, in which said interconnection link has an elongate slot extending near but short of its respective longitudinal ends, said first and second lock-bolt connections being via the slot of said interconnection link.

5. An osteosynthesis device for external fixation of a bone, comprising a central multi-part body of variable length between spaced ends of said body, first and second bone-pin or screw clamps having a releasably lockable ball-joint connection to the respective ends of said body; said body comprising at least two arm or link members, each of which has an elongate slot, and a lock bolt through the slot of each of two of said arm or link members, for releasably locked retention of said link members in a selected position of adjusted angular relation and overall length; said lock bolt comprising a shank of length to exceed passage through the slot of each of two arm or link members to be connected, a head at one end of the shank and of diametral extent exceeding the width of the arm or link-member slot adjacent thereto, said shank having a cylindrical portion extending through the thickness of the arm or link member adjacent said head, said shank being enlarged and configured distally of said cylindrical portion for keying engagement with at least a portion of the other arm or link member and distally projecting beyond said other arm or link member; and locking means including a seating washer of width exceeding the slot width of the other arm or link member with the distal end of said shank projecting beyond said seating washer, a transverse rotatable pin that is centrally engaged to the distally projecting end of said shank and that has cylindrical bearing portions eccentric to the central engagement, said bearing portions riding diametrically opposite portions of said washer.

6. An osteosynthesis device according to claim 5, wherein the slots extend along substantially the entire length of each of said arm or link members.

7. An osteosynthesis device according to claim 5, wherein said central engagement is via a transverse bore in the distally projecting end of said shank.

8. An osteosynthesis device according to claim 5, wherein said washer has a central opening configured for keying engagement to the distal end of said shank.

9. An osteosynthesis device according to claim 5, wherein diametrically opposed concave cylindrically arcuate bearing portions of said washer are configured for rotatable location and support of the cylindrical bearing portions of said pin.

10. An osteosynthesis device according to claim 5, in which the number of arm or link members is three, first and second of said arm or link members providing the respective ends of said body, and the third arm or link member having a first lock-bolt connection to said first arm or link member and having a second lock-bolt connection to said second arm or link member.

* * * * *